United States Patent [19]

Ohashi et al.

[11] 4,178,223
[45] Dec. 11, 1979

[54] ELECTRICAL OXYGEN PROBE

[75] Inventors: Minoru Ohashi; Youichi Ishikawa; Makoto Shouda; Tamon Watabe, all of Tokyo, Japan

[73] Assignee: Oriental Yeast Co., Ltd., Tokyo, Japan

[21] Appl. No.: 902,840

[22] Filed: May 4, 1978

Related U.S. Application Data

[63] Continuation of Ser. No. 815,278, Jul. 13, 1977, abandoned.

[51] Int. Cl.² ............................................. G01N 27/46
[52] U.S. Cl. ............................... 204/195 P; 204/1 T
[58] Field of Search ............................ 204/1 P, 195 P

[56] References Cited

U.S. PATENT DOCUMENTS

| | | | |
|---|---|---|---|
| 3,098,813 | 7/1963 | Beebe et al. | 204/195 P |
| 3,334,623 | 8/1967 | Hillier et al. | 204/195 P |
| 3,689,394 | 9/1972 | Davies et al. | 204/195 P |
| 3,700,579 | 10/1972 | Clifton et al. | 204/195 P |
| 3,764,504 | 10/1973 | Arff et al. | 204/195 P |
| 3,957,612 | 5/1976 | Niedrach et al. | 204/195 P |
| 3,985,633 | 10/1976 | Lubbers et al. | 204/195 P |

Primary Examiner—T. Jung
Attorney, Agent, or Firm—Stevens, Davis, Miller & Mosher

[57] ABSTRACT

An electrical membrane probe for the measurement of dissolved oxygen concentration in fluids, particularly designed for monitoring or control of fermentation process and characterized as follows;

1. The anode metal is lined on the internal wall of the electrolytic cell which is made of metal tube.
2. The vent hole for the adjustment of outer and inner pressures and the protection cover to prevent the inflow of medium into the cell are provided.
3. All of parts are connected with each other mechanically then unskilled operators can exchange the especially membrane and cathode, when some of the parts are ruptured or worn out.
4. The probe can maintain its ability even after repeated steam sterilization at high temperatures such as 130° C.
5. The deterioration of insulation is completely prevented by using glass as insulating material.
6. The membrane can be removed and exchanged easily by removing the membrane holding cap.

7 Claims, 6 Drawing Figures

FIG. 1 FIG. 2
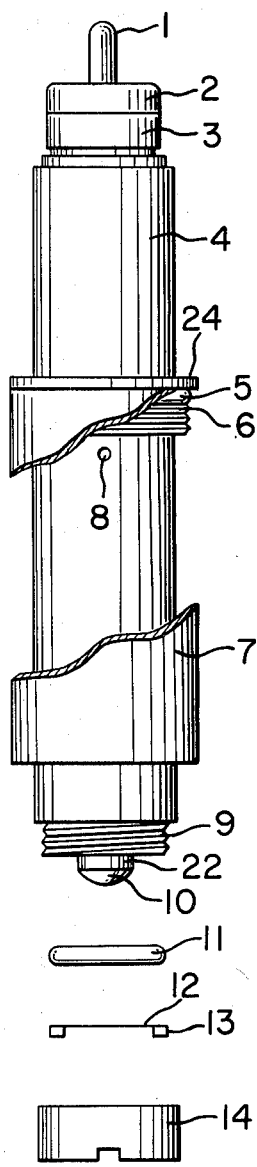
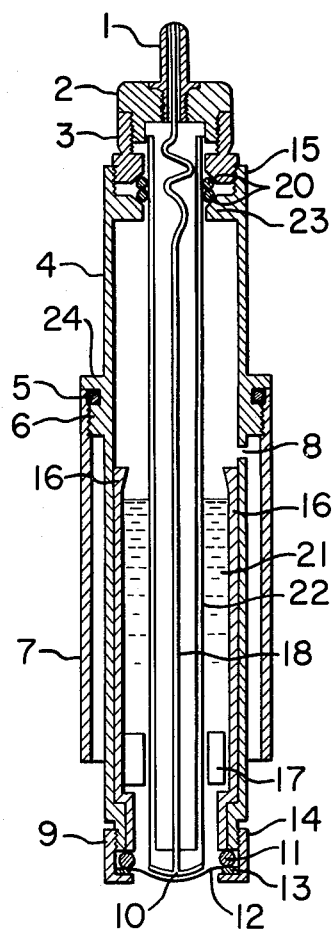
FIG. 3
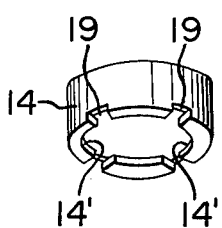

ELECTRICAL OXYGEN PROBE

This is a continuation of application Ser. No. 815,278 filed July 13, 1977, now abandoned.

BACKGROUND OF THE INVENTION

This invention relates to an electrical oxygen probe for the measurement of dissolved oxygen concentrations in fluids and of oxygen partial pressure in the air, particularly an electrical oxygen probe using a membrane electrode.

In the past for the measurement of dissolved oxygen concentration, polarographic and galvanic probes using membrane electrode were proposed. The polarographic membrane probe is provided with noble metals for both anode and cathode and requires the application of an applied voltage for the measurement of electrolytic reductive current of oxygen. The galvanic membrane probe is provided with a noble metal for cathode and a base metal for anode. Since this probe is a cell itself, no external electricity is required and the current derived from the reduction of oxygen is measured.

The prior technologies such as the said polarographic membrane probe and the said galvanic membrane probe were not sufficient in the durability for the steam sterilization which is carried out at elevated temperatures and at high pressures. Furthermore, when some parts of the probe such as membrane are raptured, the raptured parts can not be replaced for new ones. In other words, the whole probe becomes useless and a new one is required.

In general, in order to control the conditions of culture of microorganism and fermentation, it is essential, as is well known, to measure the oxygen concentration of the fermentation medium in the fermentor. However, prior to initiating the fermentation, the steam sterilization is usually carried out at the temperatures of 100° C.-120° C. Therefore it is expected that a membrane probe applicable and durable under such conditions is proposed.

In these past years, several improvements of such probes were proposed, but are not sufficient in their function yet. The reasons are that such a conventional probe is formed by individual separate parts such as an anode, a cathode and an electrolytic cell, then the structure is complicated, and that most of the said parts are connected with each other or insulated with each other by adhesives and the likes, then the connecting sections are ruptured easily by repeated sterilization at elevated temperatures and cooling in the culture and the fermentation. Furthermore, conventional probes have not sufficient durability in their materials and structures. Therefore it is difficult for users to repair probes by themselves in case that some parts of probes are ruptured. That is, such conventional probes have disadvantages in economics and operability.

For example, an improved galvanic membrane probe was reported as the title "The Value and Use of Dissolved Oxygen Measurement in Deep Culture" in the Chemical Engineer, No. 258 February 1972, p 63–71.

The outline of the art is as follows;

The essential part of the probe consists of a tubular glass body. For culture vessels of working volume greater than half a liter the glass body may be enclosed in a metal sheath. A PTFE (Teflon) membrane, 0.002 in thick, is sealed to one end with adhesive and held in position with a sleeve of silicone tube. The circular disc, which the membrane presents, forms the detecting element of the probe. The other end of the tube carries (i) the terminal connection for the anode and cathode, (ii) a filling tube, and (iii) a vent tube. In immediate contact with the membrane is a silver cathode consisting of a flat spiral of silver wire. Behind the silver is an anode composed of a helical spiral of lead sheet. The electrolyte is a mixture of sodium and lead acetates and acetic acid.

The cell is not sealed. Instead the gas space above the electrolyte is vented into the head space above the culture liquid. Thus, regardless of the internal pressure in the culture vessel, and in distinction to the conditions which apply in a sealed cell, the membrane is never subjected to a differential pressure greater than that of the head of culture liquid. This pressure is applied externally so that the silver cathode supports the membrane physically. Thus damage due to bursting stresses, produced during steam sterilizing, has been eliminated.

Although lack of sealing will enable oxygen to diffuse into the cell through the surface of the electrolyte, if such diffusion does occur, surprisingly it is not manifested as a residual current. It has been proposed that the effect of such diffusion is overcome because the oxygen is consumed by reaction with the upper part of the lead anode.

The silver-lead cell was chosen because the residual current at zero oxygen tension is small.

The electrolyte is of special composition as follows:

| | |
|---|---|
| Acetic acid | 5.0 M |
| Sodium acetate | 0.5 M |
| Lead acetate | 0.1 M |
| pH value | 3.0 approx. |

Heating the probe to a temperature above the atmospheric boiling point imposes the need to take precautions during the cooling process.

Although the probe is designed to withstand repeated steam sterilization it can be damaged if it is not steam sterilized properly.

A probe in a culture vessel which is steamed in situ is never at risk, whether the vessel is empty or charged with medium, if at the end of steam treatment and during cooling, sterile air is introduced into the vessel to maintain a minimum total pressure, $P_m$, which never falls below atmospheric, and is always greater than the corresponding aqueous vapour pressure, $P_a$, of the culture medium or of the electrolyte in the probe. Thus evaporation and boiling are prevented. This is a routine practice designed to prevent concentration of the culture medium and, after the culture has cooled to below 100° C., to prevent the ingress of contaminated ambient air, and the risk of mechanical collapse of the vessel, due to formation of a vacuum.

There is no risk if a laboratory vessel is sterilised in an autoclave of modern design which has provision for adding air under pressure during the cooling cycle in the manner described above.

The risks associated with cooling in an atmosphere of steam alone will now be discussed. If during cooling steam pressure falls too rapidly so that $P_a < P_m$ then water will evaporate or the electrolyte may even boil or bump out of the probe. If enough electrolyte is ejected so that the lead anode is not immersed the probe will not work. If the loss of electrolyte is partial so that the lead protrudes above the surface then after a few weeks the anode will break at the electrolyte surface. Again the probe will not work. If this method is employed then a probe should never be sterilized unless it is immersed in a bulk of medium or water, the time to cool to 100° C. should be adjusted so that it is never less than 15 to 30 min. and the autoclave air vent should never be opened until the pressure has fallen to less than atmospheric.

Significant evaporation of water is an inevitable feature of this method of cooling and so there will be a cumulative loss of water during successive sterilizations. This will shorten probe life and change calibration conditions. Thus it will be seen that reliable operation, whether by treatment in situ or in an autoclave, is only possible if an air supply is used to minimise evaporation.

Having prevented boiling during cooling, it will be found that, for an initial treatment, one hour's exposure is sufficient. In subsequent use providing that the probe is never put on open circuit, the treatment time dictated by the needs of medium sterilization will generally be satisfactory.

The probe can be used for 30 to 40 batch cultures at 0.21 atm oxygen tension, each involving sterilization of the probe, before the output of current deteriorates to an unacceptable level. It is found that deterioration was rapid after the 28th sterilization.

The method of internal balancing, by exposing the vent hole to the gas space above a culture, puts a probe at risk if the culture foams. Medium may then enter the vent and gain access to the electrolyte. This risk is real in the case of the glass bodied type. In the shrouded variety where the glass body is encapsulated in a steel pipe there is a large internal capacity for foam. If foaming does occur there is a little risk of foam diluting the electrolyte, by gaining access through the secondary vents in the glass body.

The fragile nature of the membrane requires that the magnitude and direction of application of any pressure difference to which it is exposed shall be controlled. As a general rule the pressure outside the probe should be greater than the internal pressure. The silver cathode then acts as a support for the membrane. This improves dimensional stability and contributes to consistency of calibration. Experience has shown that, to reduce the risk of membrane rupture, it is unwise to immerse a probe, vented to the airspace in the vessel, to a greater depth than 10 ft of medium. That is, the recommended safe working pressure difference is 5 lbf in$^2$. It is also axiomatic that the pressure difference should be held at a constant value to maintain dimensional and hence calibrational stability.

The said membrane probe requires a big membrane which is fixed at the bottom of glass tube and the area of which is about 10 times big as that of the glass tube bottom. The excess parts of the membrane is put on the glass tube wall and tightened by a silicon sleeve. Finally, the membrane is protected by covering a socket of stainless steel tube.

Accordingly, in cases that (a) the membrane is ruptured or loosened, (b) the activity and the output is lowered because of the stain of the cathode surface, (c) the electrolyte is spoiled, (d) the electrolyte is boiled off and reduced in the steam sterilization, the membrane probe cannot withstand to be used and a new one is required.

SUMMARY OF THE INVENTION

An object of this invention is to provide an improved electrical oxygen probe, eliminating the said disadvantages of conventional arts. Especially, according to this invention in cases of the said (a) (b) (c) (d), the membrane probe is easily repaired. In other word, an object of this invention is to provide an electrical oxygen probe which is used repeatedly, of which the membrane is easily removed or exchanged, of which the cathode surface is cleaned and of which the electrolyte is refilled up or exchanged.

Another object of this invention is to provide an electrical oxygen probe of which the structure is simple and then of which the cathode is easily exchanged.

A further object of this invention is to provide an electrical oxygen probe which withstands to be used under the conditions of pressurized steam sterilization and which is suitable to be used for the measurement of dissolved oxygen concentration in a culture vessel or a fermentor.

This invention provides the following probe;

1. An electrical oxygen probe in a galvanic or polarographic membrane probe for the measurement of dissolved oxygen concentration in a liquid which comprises a cathode, an anode, an oxygen permeable membrane, an electrolyte and an electrolytic cell, wherein an anode metal which constitutes the said anode is lined on the internal wall of the said electrolytic cell from the bottom to a suitable height.

2. An electrical oxygen probe as defined in 1 wherein the said electrolytic cell is a metal tube, at the top of which an internal screw thread and an internal flange below the said thread are provided, in the center of which an external screw thread, an external flange above the said thread and a vent hole below the said thread for the adjustment of inner and outer pressures are provided, at the bottom of which an external screw thread is provided.

3. An electrical oxygen probe as defined in 1, wherein the electrolytic cell contains an electrolyte and in the center of which a protection cover is screwed to the said cell and is compressed to a o-ring and the said external flange.

4. An electrical oxygen probe as defined in 1, wherein the said cathode is comprised of a glass tube and a lead wire, wherein the lead wire is a noble metal and one of the terminals is soldered with the bottom of the said glass tube and the other is placed at the top of probe through the said glass tube.

5. An electrical oxygen probe as defined in 1, wherein the said glass tube is kept in the center of the said electrolytic cell by clamping the upper part of the said glass tube with o-rings which are compressed between a plug and a flange.

6. An electrical oxygen probe as defined in 1, wherein the said oxygen permeable membrane is sticked on the bottom of the said electrolytic cell by clamping with a o-ring, a washer and a cap, wherein the said membrane contacts with the surface of the said cathode.

7. An electrical oxygen probe as defined in 1, wherein the said cap is provided with grooves to eliminate foam.

8. An electrical oxygen probe in a galvanic or polarographic membrane probe which comprises a cathode, an anode, an oxygen permeable membrane, an electrolyte and an electrolytic cell, which is characterized as follows;

(i) the said electrolytic cell is a metal tube, at the top of which an internal screw thread and an internal flange below the said thread are provided, in the center of which an external screw thread, an external flange above the said thread and a vent hole below the said thread for the adjustment of inner and outer pressures are provided, at the bottom of which an external screw thread is provided.

(ii) the said anode is that an anode metal is lined on the internal wall of the said electrolytic cell from the bottom to a suitable height.

(iii) the said cathode is comprised of a glass tube and a lead-wire, wherein the said lead-wire is a noble metal and one of the terminals is soldered with the bottom of the said glass tube and the other is placed at the top of probe through the said glass tube.

(iv) the said oxygen permeable membrane is sticked on the bottom of the electrolytic cell by clamping with a O-ring, a washer and a cap having several grooves to eliminate foam, wherein the said membrane contacts with the surface of the said cathode.

(v) the said glass tube is kept in the center of the said electrolytic cell by clamping the upper parts of the said glass tube with O-rings which are compressed between a plug and a flange.

(vi) the said electrolytic cell contains an electrolyte and in the center of which a protection cover is screwed to the said cell and is compressed to a O-ring and the said external flange.

BRIEF DESCRIPTION OF THE DRAWINGS

FIG. 1 is a side view of the electrical oxygen probe of this invention with sectional views partially.

FIG. 2 is a cross-sectional side elevational view of the electrical oxygen probe of this invention.

FIG. 3 is a squint view of a cap for the holding of membrane. 1. cathode terminal 2. insulation 3. anode terminal 4. electrolytic cell 5. O-ring 6. external screw thread for protection cover 7. protection cover 8. vent hole 9. external screw thread for membrane holding cap 10. cathode metal (cathode) 11. O-ring 12. oxygen permeable membrane 13. washer 14. membrane holding cap 14'. edge 15. internal screw thread for plug 16. anode metal (anode) 17. cathode guide 18. lead-wire 19. foam eliminating groove 20. O-ring 21. electrolyte 22. glass tube 23. internal flange 24. external flange

PREFERRED EMBODIMENT OF THE INVENTION

Figure 4:
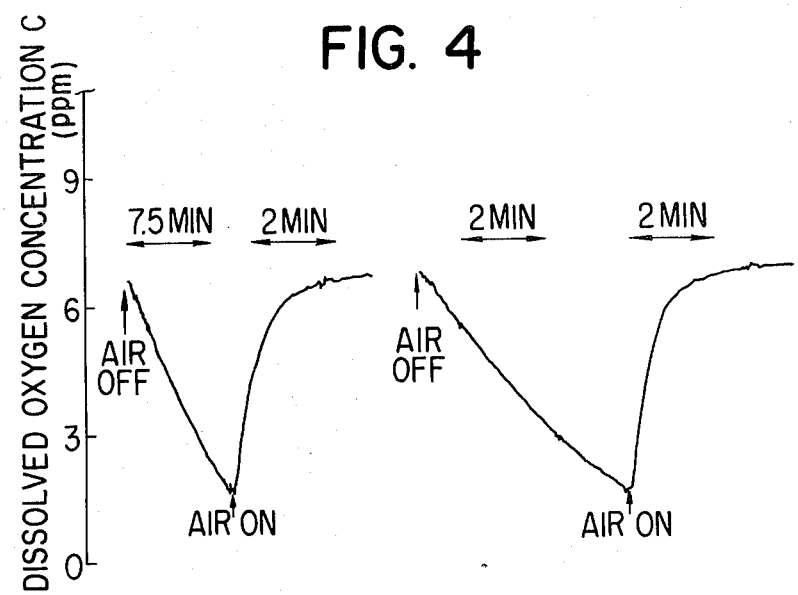
FIG. 4 shows the concentration of dissolved oxygen in the dynamic method. (Strain: Saccharomyces cerevisiae, aeration rate=330 ml/min, agitation speed=500 rpm, working volume=1.3 l)

Referring to the drawings, an electrical oxygen probe of this invention is described in detail. An electrolytic cell 4 is a metal tube made of such as stainless steel, having an internal screw thread 15 for a plug and an internal flange 23 below the said screw thread at the top of the tube, at the center of the tube an external flange 24 and an external screw thread 6 below the said flange for a protection cover and a vent hole 8 below the screw thread for the adjustment of outer and inner pressures, and at the bottom of the tube an external screw thread 9 for a membrane holding cap. An anode metal 16 is lined on the internal wall of the said electrolytic cell 4 from the bottom to a suitable height. The anode metal is a base metal such as lead for a galvanic probe and a noble metal such as silver for a polarographic probe. As for the lining methods of anode metals, there are a conventional plating method and a method that an anode metal is poured into the said cell and becomes solid with cooling and then a small hole is drilled. The upper end of anode metal lining may be above or below the vent hole 8 and may reach the internal flange 23.

A cathode section has a cathode metal 10 which is of noble metal such as platinum, gold, and silver soldered on the bottom of a glass tube 22, and a lead-wire which connects between the soldered part and the external cathode terminal. The lead wire may be of noble metal. The said glass tube 22 is kept in the center of the cell 4, by being clamped with a plug and O-ring 20. If required, cathode guides 17 are provided.

An oxygen permeable membrane 12 such as Teflon is sticked on the head of the cell 4 by compressing with O-ring 11 and washer 13 and by screwing with a membrane holding cap 14 in order to contact with the cathode 10 of the glass tube. There are several alternative methods for sticking the membrane. For example, it is convenient that a membrane is adhesived previously to the washer 13. It is preferred that the membrane holding cap 14 is provided with several foam eliminating grooves 19 as shown in FIG. 3 to avoid the retention of foams. 2 is an insulation, 1 is a cathode terminal connecting with a lead-wire. 3 is an anode terminal connecting with an electrolytic cell. A plug is consistent of 1, 2 and 3.

A protection cover 7 is made of a metal tube such as stainless and is screwed to an external screw 6 of the cell 4 and is kept closely with the cell 4 by being compressed with O-ring 5 and an external flange 24.

An electrolyte is a conventional one such as an aqueous solution of 2% caustic soda or caustic potassium. It is filled in the internal space formed among an anode 16, a glass tube 22 and an oxygen permeable membrane.

As mentioned above, an electrical oxygen probe of this invention for fermentation has a simple structure due to the electrolytic cell is itself equipped with flanges, screws and the likes and assumes to be the main structure.

Especially, as the anode section is lined on the internal wall of the cell directly, neither anode space nor anode lead-wire are required. It makes the internal cell space very huge. Accordingly, it becomes easy to install the cathode section and it eliminates troubles such as that the cathode section is likely to be ruptured by striking the adjacent part when an external shock is happened.

Furthermore the electrical oxygen probe for fermentation in accordance with this invention can keep the outer and inner pressures of the cell same through a vent hole. It eliminates the pressure difference between the outer and inner of the membrane. The protection cover prevents the examined solution from flowing into the cell through the vent hole when the probe is submerged in a fermenting solution.

Another advantage of this invention is that as this probe does not use adhesives to combine each part and employs screw connecting in all section, there is no trouble such as disconnecting or disinsulation even though it is applied repeatedly under the conditions of heat sterilization and cooling.

Furthermore as this probe is constructed simply, it is easy to maintain, to check and to exchange parts which is weared or ruptured. For example, as for the membrane, it is removed and exchanged easily by removing the membrane holding cap. As for the cathode section, it is exchanged easily by removing the plug. Therefore the invented probe is a very economical device because it is maintained and repaired easily without any special experience.

Moreover, depending on the various applications of the probe, it is easily possible to adopt a membrane of adequate thickness, selected from thick to thin, because the exchange of the membrane is very easy.

EXAMPLE 1

Sterilizing test in the autoclave

An electrical oxygen probe in accordance with this invention is used repeatedly for the measurement of dissolved oxygen concentration in an autoclave under the similar conditions to fermentation sterilization.

| Probe: | |
|---|---|
| Cell | Galvanic cell having an external cylinder made of stainless steel, as shown in FIGS. 1-3. |
| Anode | lead |
| Cathode | platinum |
| Membrane | FEP (Fluorinated Ethylene Propylene copolymer) film (0.05 mm in thickness) |
| Electrolyte | 2% sodium hydroxide aqueous solution |

The results are shown in the following table.

| Autoclaving condition: | |
|---|---|
| Autoclave | HA-30 (Hirayama Seisakusho, Japan) |
| Gauge pressure | 1.2 kg/cm$^2$ |
| Temperature | 120° C. |
| Sterilization time | 30 min. |
| Cool down time | 30 min. |
| Measurement: | |
| Diffusion current | measured in the air saturated water (PO$_2$ = 0.21 atm) at 30° C. |
| Residual current | measured in 5% Na$_2$SO$_3$ solution (PO$_2$ = 0 atm) at 30° C. |
| Response time | transferred from air saturated water (PO$_2$ = 0.21 atm) to 5% Na$_2$SO$_3$ soln. at 30° C. |

Table 1

| Times of sterilization | Diffusion current (μA) | Residual current (μA) | 90% Response Time (sec) | |
|---|---|---|---|---|
| 1 | 8.60 | 0.03 | 30 | |
| 2 | 7.40 | 0.00 | 28 | |
| 3 | 9.48 | 0.40 | 72 | |
| 4 | 9.22 | 0.02 | 28 | |
| 5 | 8.11 | 0.00 | 30 | |
| 6 | 8.30 | 0.58 | 35 | |
| 7 | 7.25 | 0.62 | 50 | |
| 8 | 8.00 | 0.00 | 68 | |

Table 1-continued

| Times of sterilization | Diffusion current (μA) | Residual current (μA) | 90% Response Time (sec) | |
|---|---|---|---|---|
| 9 | 9.28 | 0.18 | — | electrolyte was added |
| 10 | 9.61 | 0.32 | 40 | |
| 11 | 7.72 | 0.38 | 47 | |
| 12 | 7.92 | 0.38 | 74 | |
| 13 | 9.40 | 0.15 | 52 | |
| 14 | 11.80 | — | 46 | |
| 15 | 5.85 | 0.30 | 94 | |
| 16 | 7.85 | 0.55 | 78 | |
| 17 | 8.45 | 0.76 | 118 | |
| 18 | 10.50 | — | 36 | membrane and electrolyte were changed |
| 19 | 9.01 | 0.25 | 39 | |
| 20 | 10.50 | 0.58 | 51 | |
| 21 | 10.00 | 0.40 | 52 | |

EXAMPLE 2

Sterilizing Test in 30 l Jar Fermentor (1) Steam sterilization in empty fermentor
Sterilization condition:
The sensor was installed on the side wall of the fermentor.

| Temperature | 100° C. |
|---|---|
| Time | 30 min. (at 100° C.) |
| Cool down time | 60 min. (down to 31° C.) |

Repeated sterilization was carried out for 3 times under the above condition.
The results are shown in the following table.

Table 2

| | Diffusion current in air saturated water (30° C.) | | 90% Response Time at 30° C. in air saturated water | |
|---|---|---|---|---|
| Sensor No. | before (μA) | after (μA) | before (sec) | after (sec) |
| 1 | 10 | 9 | 36 | 36 |
| 2 | 9 | 9.5 | 25 | 23 |

(2) Steam sterilization in the fermentor charged with medium
Sterilization condition:
The same sensor as above mentioned was used. Repeated sterilization was carried out for 5 times under the same condition as described above.
The results are shown in the following table.

Table 3

| | Diffusion current in air saturated water (30° C.) | | 90% Response Time at 30° C. in air saturated water | |
|---|---|---|---|---|
| Sensor No. | before (μA) | after (μA) | before (sec) | after (sec) |
| 1 | 9 | 9 | 36 | 39 |
| 2 | 9.5 | 9 | 23 | 21 |

EXAMPLE 3

Estimation of specific respiration rate ($Q_{O_2}$) and volumetric oxygen transfer coefficient ($k_L a$) : "Dynamic Method"

Strain used: *Saccharomyces cerevisiae*

Medium composition:
 Glucose: 5 g
 KH₂PO₄: 2 g
 (NH₄)₂SO₄: 1 g
 MgSO₄7H₂O: 0.2 g
 Yeast extract: 1 g
 Distilled water: 1 l
Operational condition:
 aeration rate=330 ml/min
 agitation speed=500 rpm
 operational volume=1.3 l
 temperature=30° C.
Jar fermentor: IWASHIYA K. SAWADA CO. LTD.
 Type MB (nominal volume=2 l).
Membrane used in the probe: FEP film(0.025 mm in thickness)

The measurement was conducted during the log phase ($\mu=0.2$ hr$^{-1}$) while the cell concentration was 0.64 g/l.

1-A: Estimation of $Q_{O2}$ value from the slope when the air supply is off.

$$Q_{O2} = 55.5 \ \mu g \ oxygen/hr \ mg \ dry \ cell$$
$$= 1.73 \ mmol \ oxygen/hr \ mg \ dry \ cell$$

1-B: Estimation of $k_La$ value and saturation concentration of oxygen in the medium, $C^*$.

Figure 5:
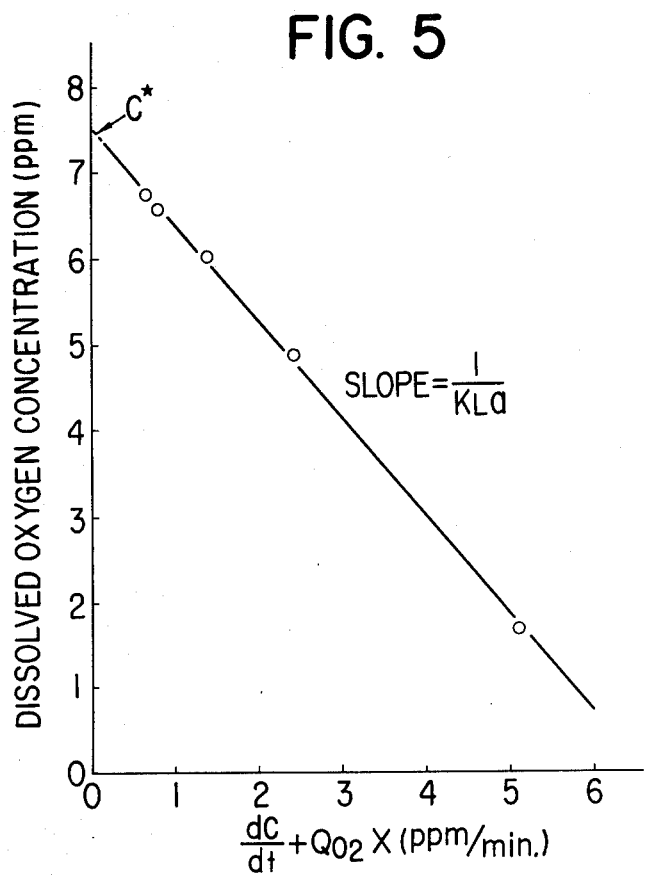
FIG. 5 is a graph showing the relationship between dissolved oxygen concentration and $(dC/dt)+Q_{O_2}X$ for the estimation of values, $C^*$ (saturation concentration of oxygen in the medium) & $k_La$ (volumetric oxygen transfer coefficient)

Dissolved oxygen concentration, C vs. $\frac{dc}{dt} + Q_{O2}X$
which are calculated from the slope of the
FIG. 4 when the air is on is shown in FIG. 5.
$C^* = 7.5$ ppm
$k_La = 0.91$ min$^{-1}$

| | $k_La$ (min$^{-1}$) |
|---|---|
| Dynamic method | 0.91 |
| Sulfite oxidation method** | 0.99 |

**Sulfite oxidation method was used in the same operational condition except that the medium was replaced by distilled water.

EXAMPLE 4

Stability test in the continuous cultivation using phenol-utilizing yeast.

| Strain used: *Trichosporon cutaneum* | |
|---|---|
| Medium compositions: | |
| NH₄Cl | 5 g |
| KH₂PO₄ | 2.5 g |
| MgSO₄7H₂O | 1 g |
| CaCl₂2H₂O | 10 mg |
| FeCl₃6H₂O | 10 mg |
| Biotin | 2 μg |
| Ca-Pantothenate | 400 μg |
| Inositol | 2000 μg |
| Nicotinic acid | 400 μg |
| P-Aminobenzoic acid | 200 μg |
| Pyridoxine HCl | 400 μg |
| Thiamine HCl | 400 μg |
| Riboflavine | 200 μg |
| Distilled water | 1 l |
| Phenol 200-400 mg | (feeding concentration) |
| Operational condition: | |
| aeration rate = 300 ml/min | |
| agitation speed = 700 rpm | |
| operational volume = 1.2 l | |
| temperature = 30° C. | |
| dilution rate = 0.1 (hr$^{-1}$) | |
| Jar fermentor: | |
| IWASHIYA K. SAWADA CO. LTD. | |
| Type MB (nominal volume = 2 l) | |

The chart indicates that the oxygen probe is working fairly stably for more than 100 hrs in the specific degradation of phenol with the continuous culture.

Figure 6:
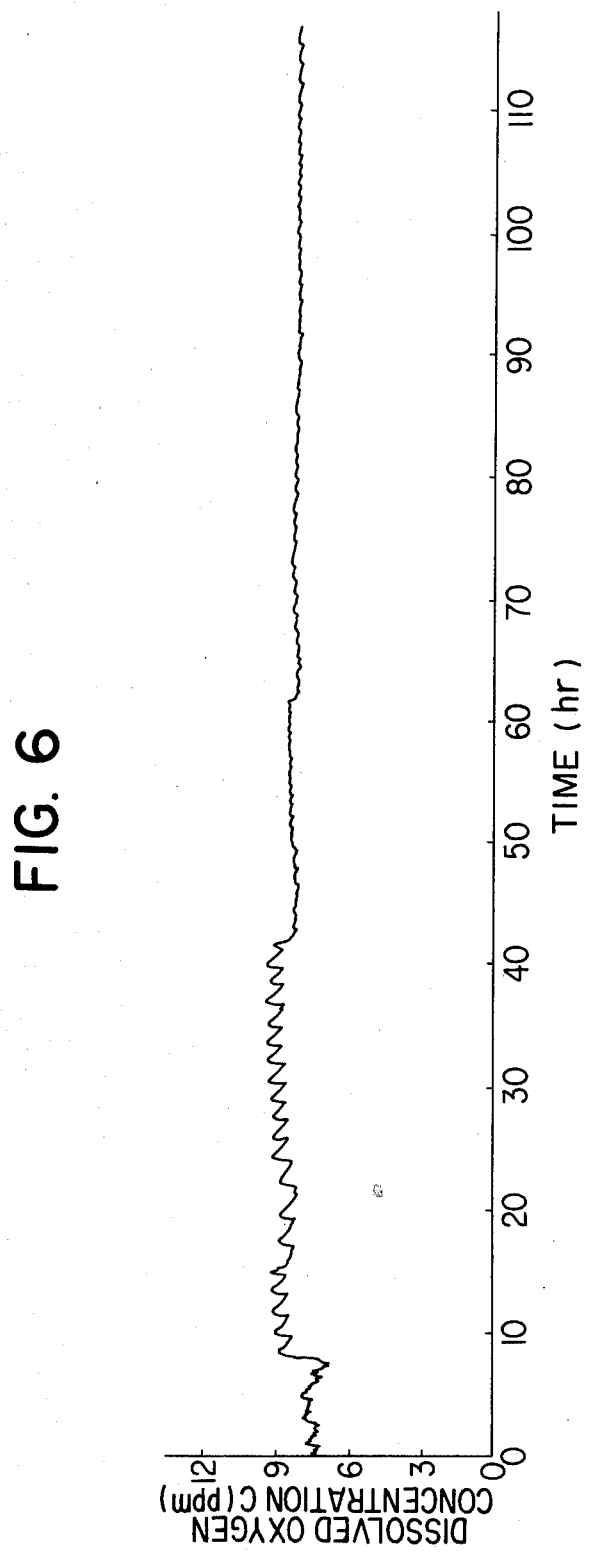
FIG. 6 shows the results of the stability test of the oxygen probe for the continuous cultivation of phenol-utilizing yeast, Trichosporon cutaneum. (aeration rate=300 ml/min, agitation speed=700 rpm, working volume=1.2 l, dilution rate=0.1 $(hr^{-1})$) Feeding concentration of phenol=273 mg/l, steady state concentration of phenol=5 mg/l.

Periodical changes observed in the beginning are the reflection of temperature change in the jar fermentor because the temperature was coarsely controlled (deviation is ±1° C.), while fine temperature control established later gives less fluctuated results as shown in FIG. 6.

What is claimed are:

1. An electrical oxygen probe in a galvanic membrane probe which comprises a cathode, an anode, an oxygen permeable membrane, an electrolyte and an electrolytic cell wherein:
 (i) said electrolytic cell is a metal tube, at the top of which an internal screw thread and an internal flange below the said thread are provided, in the center of which an external screw thread is provided, an external flange above the said thread and a vent hole below the said external thread for the adjustment of inner and outer pressures are provided, at the bottom of which an external screw thread is provided;
 (ii) a metal which constitutes the anode is lined on the internal wall of the said electrolytic cell from the bottom to a suitable height;
 (iii) the said cathode is comprised of a metal disposed at one end of a glass tube and a lead wire connected at one end to the cathode metal and extending through the glass tube at the other end;
 (iv) the said oxygen permeable membrane is sticked on the bottom of the electrolytic cell by clamping with a O-ring, a washer and a cap having several grooves to eliminate foam, wherein the said membrane contacts with the surface of the said cathode;
 (v) the said glass tube is kept in the center of the said electrolytic cell by clamping the upper parts of the said glass tube with O-rings which are compressed between a plug and said internal flange; and
 (vi) the said electrolytic cell contains an electrolyte and in the center of which a protection cover is screwed to the said cell and is compressed to a O-ring and the said external flange.

2. An electrical oxygen probe in a galvanic membrane probe for the measurement of dissolved oxygen concentration in a liquid, which comprises a cathode, an anode, an oxygen permeable membrane, a vent hole, an electrolyte and an electrolyte cell,
 the electrolytic cell being an elongated cylindrical tube containing said cathode in the center,
 said cathode comprising a glass tube and a lead wire one terminal of which is connected with a cathode metal at the bottom of said glass tube and the other terminal of which is located at the top of the probe through the glass tube,
 the inner wall of the electrolytic cell being lined with an anode metal from the bottom to a suitable height below said vent hole for adjusting inner and outer pressures,
 the electrolyte being filled between the glass tube of the cathode and the anode in the electrolytic cell, and
 the oxygen permeable membrane attached to the bottom of the electrolytic cell by an O-ring, a washer, and a membrane holding cap, wherein said membrane contacts the surface of the cathode metal through a thin electrolyte layer.

3. An electrical oxygen probe as defined in claim 2, wherein the said electrolytic cell is a metal tube, at the top of which an internal screw thread and an internal flange below the said internal thread are provided, in the center of which an external screw thread is provided, an external flange above the said external thread and at the bottom of which an external screw thread is provided.

4. An electrical oxygen probe as defined in claim 2, wherein a protection cover is screwed to the said cell at the first mentioned external thread.

5. An electrical oxygen probe as defined in claim 2, wherein said glass tube is kept in the center of the said electrolytic cell by clamping the upper part of the said glass tube with O-rings which are compressed between a plug and a flange.

6. An electrical oxygen probe as defined in claim 2, wherein the said cap is provided with grooves to eliminate foam.

7. An electrical oxygen probe as defined in claim 2, wherein the lead wire is made of a noble metal.

* * * * *